United States Patent
Maeda et al.

(10) Patent No.: US 10,444,207 B2
(45) Date of Patent: Oct. 15, 2019

(54) LIQUID CHROMATOGRAPH ANALYZER CONTROL SYSTEM

(71) Applicant: SHIMADZU CORPORATION, Kyoto-shi, Kyoto (JP)

(72) Inventors: Yoshiaki Maeda, Kyoto (JP); Yoshihiro Hayakawa, Ibaraki (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 101 days.

(21) Appl. No.: 14/964,759

(22) Filed: Dec. 10, 2015

(65) Prior Publication Data

US 2017/0168028 A1 Jun. 15, 2017

(51) Int. Cl.
*G01N 30/88* (2006.01)
*G01N 30/86* (2006.01)
*G01N 30/32* (2006.01)

(52) U.S. Cl.
CPC ......... *G01N 30/88* (2013.01); *G01N 30/8658* (2013.01); *G01N 30/8662* (2013.01);
(Continued)

(58) Field of Classification Search
CPC ............ G01N 30/88; G01N 2030/027; G01N 35/00584; G01N 35/00594;
(Continued)

(56) References Cited

U.S. PATENT DOCUMENTS 5,695,718 A * 12/1997 Imai ................. G01N 35/00594
340/521

2005/0033527 A1 * 2/2005 Wada ..................... G01D 3/08
702/35
(Continued)

FOREIGN PATENT DOCUMENTS

| JP | 2006-208099 A | 8/2006 |
|---|---|---|
| JP | 2012189552 A | 10/2012 |
| JP | 2012233798 A | 11/2012 |

OTHER PUBLICATIONS

Chromatography Forum; Wayback Machine Snapshot, Nov. 2010; https://www.chromforum.org/viewtopic.php?t=14046 (Year: 2010).*

(Continued)

*Primary Examiner* — Eric S. McCall
*Assistant Examiner* — Timothy P Graves
(74) *Attorney, Agent, or Firm* — Sughrue Mion, PLLC

(57) ABSTRACT

An analyzer control system 20 for monitoring and controlling an analyzer 20 includes: a plurality of sensors for detecting the condition of each component of the analyzer; a potential problem inference section 23 for receiving detection results obtained with all or part of the sensors and for inferring whether or not the analyzer is in a potentially problematic condition; and a potential problem display section 32 for showing, on a display screen, information on the potentially problematic condition. The "potentially problematic condition" is neither a condition in which the analysis data being collected by the analyzer are unusable, nor a condition which requires deactivation of the analyzer; it is a condition in which the analyzing operation may be continued for the time being, although the analyzer is likely to soon fall into the aforementioned situations if the operation is further continued. The already collected data can be properly used.

19 Claims, 3 Drawing Sheets

(52) U.S. Cl.
CPC .............. *G01N 2030/324* (2013.01); *G01N 2030/8804* (2013.01)

(58) Field of Classification Search
CPC ....... G01N 35/00693; G01N 35/00603; G01N 35/00613; G01N 35/00623; G01N 35/00712
See application file for complete search history.

(56) References Cited

U.S. PATENT DOCUMENTS

| | | | | |
|---|---|---|---|---|
| 2006/0207941 | A1* | 9/2006 | Morikawa .............. | G01N 30/88 210/656 |
| 2008/0021663 | A1* | 1/2008 | Wikfors ............... | B01D 15/163 702/47 |
| 2010/0324722 | A1* | 12/2010 | Fritchie ............ | G01N 35/00732 700/214 |
| 2012/0283980 | A1* | 11/2012 | Suga ................ | G01N 35/00871 702/108 |

OTHER PUBLICATIONS

Communication dated Aug. 9, 2016, from the Japanese Patent Office in counterpart application No. 2013-118970.

* cited by examiner

Fig. 5

| MONITORING INFORMATION | |
|---|---|
| Unit | |
| Pump | |
| Monitoired liquid-supply pressure | 100 MPa |
| Monitored pulsation | 0.20 MPa |
| Right plunger position | --------< |
| Left plunger position | ----> |
| Injector | |
| Monitored pressure in "Inject" phase of high-pressure valve | 100 MPa |
| Monitored pressure in "Load" phase of high-pressure valve | 90 MPa |
| Momentary pressure change at sample injection | 20 MPa |
| Detector (UV) | |
| Reference energy level (initial value) | 2,000 |
| Reference energy level (current value) | 1,000 |
| Sample energy level (current value) | 500 |

Fig. 6

| SELF-DIAGNOSIS INFORMATION | | Poor Reproducibility | High Carry-over |
|---|---|---|---|
| Unit | | Self-Diagnosis Information | |
| Pump | | | |
| Monitoired liquid-supply pressure | 100 MPa | | |
| Monitored pulsation | 0.20 MPa | ▸ Bubbles seem to be present within the right pump head. | |
| Right plunger position | --------< | ▸ Sealing performance of the right check valve or left-inlet check valve seems to be decreasing. | |
| Left plunger position | ----> | | |
| Injector | | | |
| Monitored pressure in "Inject" phase of high-pressure valve | 100 MPa | | |
| Monitored pressure in "Load" phase of high-pressure valve | 90 MPa | ▸ Neelde or sample loop seems to be clogged. | |
| Momentary pressure change at sample injection | 20 MPa | ▸ Rotor or stator of the high-pressure valve seems to be wearing. | |
| Detector (UV) | | | |
| Reference energy level (initial value) | 2,000 | | |
| Reference energy level (current value) | 1,000 | ▸ No problem. | |
| Sample energy level (current value) | 500 | ▸ Detector cell seems to be contaminated. | |

LIQUID CHROMATOGRAPH ANALYZER CONTROL SYSTEM

TECHNICAL FIELD

The present invention relates to an analyzer control system having the function of monitoring the condition of an analyzer and informing users of that condition while controlling the same analyzer.

BACKGROUND ART

One example of such an analyzer is a liquid chromatograph system, which includes various units, such as a liquid-sending pump for sending a mobile phase to a column, an injector for injecting a sample into the mobile phase, an oven for maintaining the column at a predetermined temperature or varying the column temperature according to a predetermined program, and a detector for detecting the components eluted from the column. Each of those units consists of various parts. In order to generally control the operation of such a liquid chromatograph system to perform an analysis of a single sample or a sequential analysis of a plurality of samples, the liquid chromatograph system is normally provided with a control system using a computer (for example, see Patent Literature 1).

Such a control system does not merely control the operation of each component of the liquid chromatograph system; it also monitors the condition and operational status of each component through the sensors provided in those components. Upon detecting any abnormality, the system informs users of the situation or automatically deactivates the control target, i.e. the liquid chromatograph system. For example, the control system constantly monitors the pressure of the liquid-sending pump and generates a pressure-abnormality signal if the pump pressure has exceeded the predetermined level. The system also measures the amount of energy of the lamp of the detector at appropriate points in time; if the energy has decreased to the predetermined level or lower, the system informs the user that it is time to replace the lamp.

Such information on the occurrence of a problem and the replacement of a part is stored in the control system and used by field engineers or manufacturers so as to appropriately maintain the target system.

CITATION LIST

Patent Literature

Patent Literature 1: JP 2006-208099 A

SUMMARY OF INVENTION

Technical Problem

As described earlier, recent control systems collect various measurement values (e.g. the pressure of the liquid-sending pump and the energy of the detector lamp) and information (e.g. an approaching time to replace expendable parts) related to the components of the control target (i.e. an analyzer), and display the a on a screen. Those pieces of information are mainly intended for assisting in the detection of an abnormality in the relevant components of the analyzer. Accordingly, for general users, the values displayed on the screen (e.g. the pressure of the liquid-sending pump and the energy of the detector lamp) are rather useless; in most cases, they do not notice an abnormality in a value until that value rises above or falls below the predetermined threshold and triggers the action of generating an alarm or deactivating the analyzer.

If the alarm is suddenly generated in this manner, the reliability of the already collected data is lost. Furthermore, if the analyzer is suddenly deactivated after the analysis has been continued for a considerable length of time, the important data and time amounts to nothing.

The problem to be solved by the present invention is to provide an analyzer control system which informs users of an appropriate operational status of an analyzer to be controlled and provides useful information for allowing users to take precautionary measures against possible problems before the analyzer falls into a problematic state which triggers an alarm generation, system deactivation or similar action which leads to abnormalities in the data.

Solution to Problem

The present invention developed for solving the previously described problem is an analyzer control system for monitoring and controlling an operation of an analyzer, including:

a) a plurality of sensors for detecting the condition of each component of the analyzer;

b) a potential problem inference section for receiving one or more detection results obtained with all or part of the plurality of sensors and for inferring whether or not the analyzer is in a potentially problematic condition; and c) a potential problem display section for showing, on a display screen, information on the potentially problematic condition.

The analyzer control system according to the present invention has a plurality of sensors for detecting the condition of each component of an analyzer to be controlled. The potential problem inference section receives one or more detection results obtained with all or part (which may be one) of the plurality of sensors and infers whether or not the analyzer is in a potentially problematic condition. The "potentially problematic condition" is neither a condition in which the analysis data being collected by the analyzer are abnormal or unusable, nor a condition which requires deactivation of the analyzer; it is simply a condition in which the analyzing operation may be continued for the time being, although the analyzer is likely to soon fall into the aforementioned conditions if the operation is further continued. If the inference has resulted in the conclusion that the analyzer is in the potentially problematic condition, the potential problem display section shows information on that potentially problematic condition on the display screen. Based on this information, users may decide to continue the ongoing analysis or discontinue the analysis after taking some measures. In any case, the already collected data can be properly used.

The control system may constantly display, on the display screen, the one or more detection results obtained with all or part of the plurality of sensors and/or other items of information on the operational status of the analyzer, throughout the analyzing operation. In this case, the information on the potentially problematic condition is additionally displayed only when the analyzer is considered to be in a potentially problematic condition.

For example, the potential problem inference section may be configured as follows: The analyzer control system is additionally provided with an absolute allowance determiner for determining, for each of the one or more detection results obtained with all or part of the plurality of sensors in the analyzer, whether or not the result is outside a predetermined absolute allowable range, and the potential problem inference section infers that the analyzer is in the potentially problematic condition if any of the one or more detection results obtained with all or part of the plurality of sensors is outside an operationally allowable range which is more narrowly defined than the absolute allowable range.

The "absolute allowable range" used in the absolute allowance determiner is a range which is defined for each of the one or more detection results obtained with all or part of the plurality of sensors, in such a manner that, if any detection result is outside the corresponding absolute allowable range, the data being collected should be regarded as abnormal or the analyzing operation of the analyzer needs to be discontinued. In other words, if any detection result obtained with a sensor is outside this range, there will probably be a significant influence on the progress of the analyzing operation as well as the maintenance, safety and other aspects of the system. By contrast, the "operationally allowable range" is defined by way of precaution: if any detection result is outside this range, the control system merely needs to alert the user's attention without discontinuing the analyzing operation.

The analyzer control system may be configured to perform the previously described operation only when the analyzer is performing an analyzing operation. In that case, the analyzer control system should be provided with an operational status determiner for determining whether or not the analyzer is performing an analyzing operation including a preparing operation. However, it is also useful to display the information on the potentially problematic condition in other operations, such as the regular performance check or validation. Accordingly, it is preferable to additionally display the information on the potentially problematic condition during those operations.

Advantageous Effects of the Invention

The analyzer control system according to the present invention informs users of an appropriate operational status of an analyzer to be controlled and thereby allows users to take precautionary measures against possible problems before the analyzer falls into a problematic state which triggers an alarm generation, system deactivation or similar action which leads to abnormalities in the data. Accordingly, users can use the already collected data without complications. There is no waste of time, sample and other resources consumed for a long-time analysis, as well as no waste of data. Furthermore, in the case of the conventional system, the detection results obtained with all or part of the plurality of sensors in the analyzer are not presented in such a way as to allow general users to correctly understand the meaning of those results. By contrast, in the analyzer control system according to the present invention, an inference logic which includes design knowledge offered by the manufacturer of the analyzer and a wealth of maintenance knowledge acquired by field engineers can be previously stored in the potential problem inference section, which enables a wide range of everyday users to obtain a highly reliable result of the diagnosis on the operational status of the analyzer and the potentially problematic condition.

BRIEF DESCRIPTION OF DRAWINGS

FIG. 5 shows a normal monitoring information screen in the liquid chromatograph system.

FIG. 6 shows a self-diagnosis information screen showing the information on the potentially problematic condition of the liquid chromatograph system.

DESCRIPTION OF EMBODIMENTS

Figure 1:
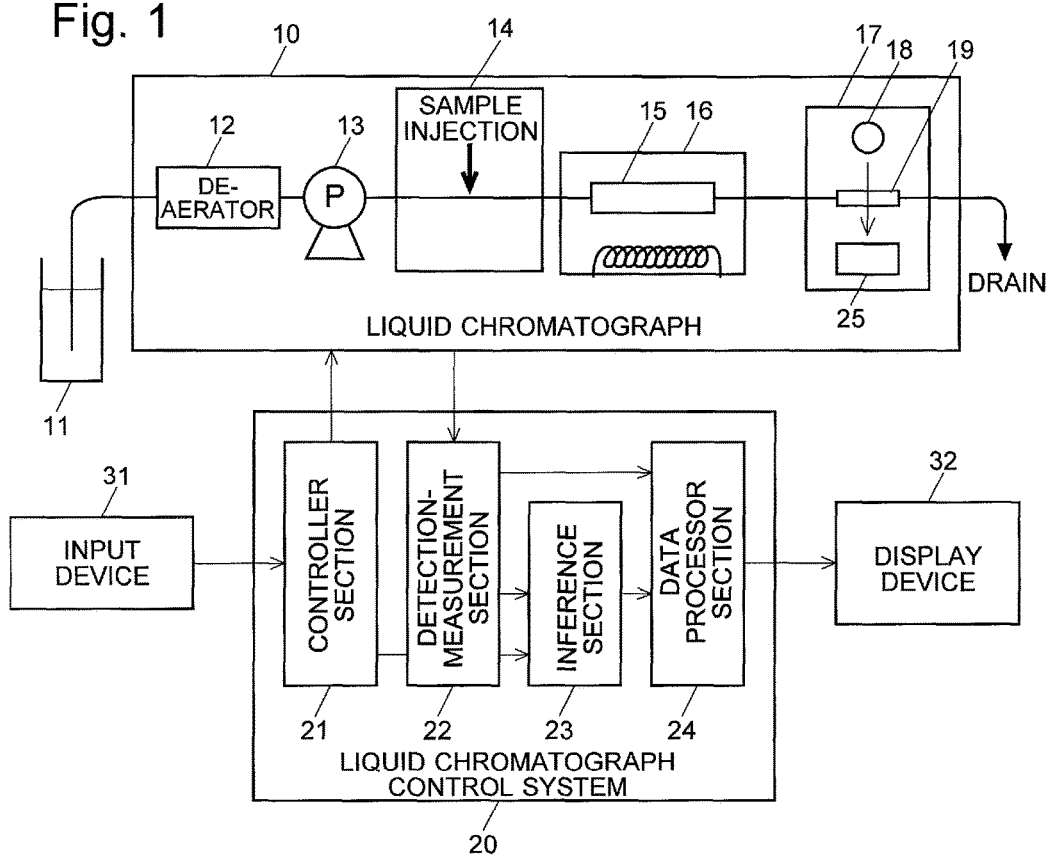
FIG. 1 is a schematic configuration diagram of a liquid chromatograph system as one embodiment of the present invention.

As one embodiment of the present invention, a liquid chromatograph control system is described. FIG. 1 is a schematic configuration diagram of a liquid chromatograph 10 and the liquid chromatograph control system 20 of the present embodiment which controls the liquid chromatograph 10 and processes the data obtained by this chromatograph. The liquid chromatograph 10 includes: a liquid-sending pump 13 for suctioning a mobile phase 11 and sending it to a column 15 at a fixed rate; a deaerator 12 for deaerating the mobile phase 11; an injector 14 for injecting a sample into the mobile phase 11 before the mobile phase 11 enters the column 15; an oven 16 for regulating the temperature of the column 15; and a detector 17 for detecting the components eluted from the column 15. An input device 31 and display device 32 are connected to the liquid chromatograph control system 20.

Figure 2:
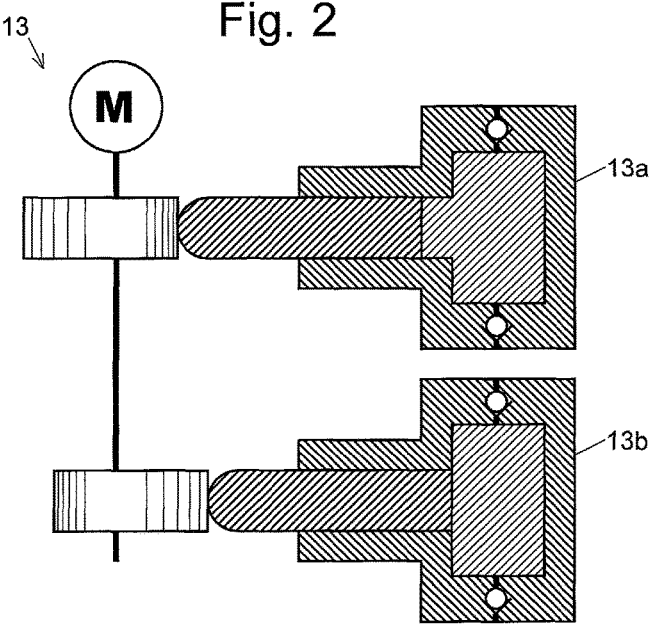
FIG. 2 a schematic configuration diagram of the liquid-sending pump in the liquid chromatograph system.

As shown in FIG. 2, the fixed-rate liquid-sending pump 13 includes a pair of (right and left) pumping units 13$a$ and 13$b$. These pumping units complementarily suction and eject the mobile phase 11 so as to send the mobile phase 11 to the column 15 at a fixed rate. The detector 17 includes a light source 18 for casting measurement light into an eluate flowing through a sample cell 19 after exiting the column 15.

Each of these sections of the liquid chromatograph 10 is provided with one or more sensors and/or measurement devices. For example, a pressure sensor for measuring the liquid-supply pressure is disposed both at the liquid-sending pump 13 and on the upstream side of the column 15. The oven 16 has a thermometer. The detector 17 includes a light-source sensor for measuring the emission energy of the light source 18 and a spectrophotometer 25 for measuring the spectrum intensity of the light which has passed through the sample cell 19.

The detection-measurement signals produced by those sensors and measurement devices are sent to a detection-measurement section 22 in the liquid chromatograph control system 20. Using the detection-measurement data, a controller section 21 in the liquid chromatograph control system 20 controls the operation of each component of the liquid chromatograph 10 according to a predetermined program, to perform an analysis of a sample. The data obtained by the analysis (e.g. the output data of the spectrophotometer 25) are sent to a data processor section 24 in the liquid chromatograph control system 20. The data processor section 24 performs various kinds of data processing and shows the obtained results on the display device 32.

The information presented on the display device 32 is not limited to the results of the analysis; the data related to the operational status of the liquid chromatograph 10, i.e. the detection-measurement data obtained with the sensors and measurement devices, are also displayed. FIG. 5 shows one example of such a display screen, in which the monitored value of the supply pressure of the liquid-sending pump 13 and the monitored values of the pressure in the high-pressure valve in the injector 14 are displayed. Such a function of displaying the data on the operational status belongs to the prior art.

The liquid chromatograph control system 20 according to the present embodiment is characterized in that an inference section 23 is provided. While the liquid chromatograph 10 is performing an analyzing operation, the inference section 23 constantly receives the detection-measurement data from the detection-measurement section 22 and infers whether or not the liquid chromatograph 10 is in a potentially problematic condition, based on the temporal change in each of the detection-measurement data and/or based on the combination of two or more of those data. The information about whether or not the liquid chromatograph 10 is performing the analyzing operation is held in the controller section 21. This information is also given to the inference section 23.

Figure 3:
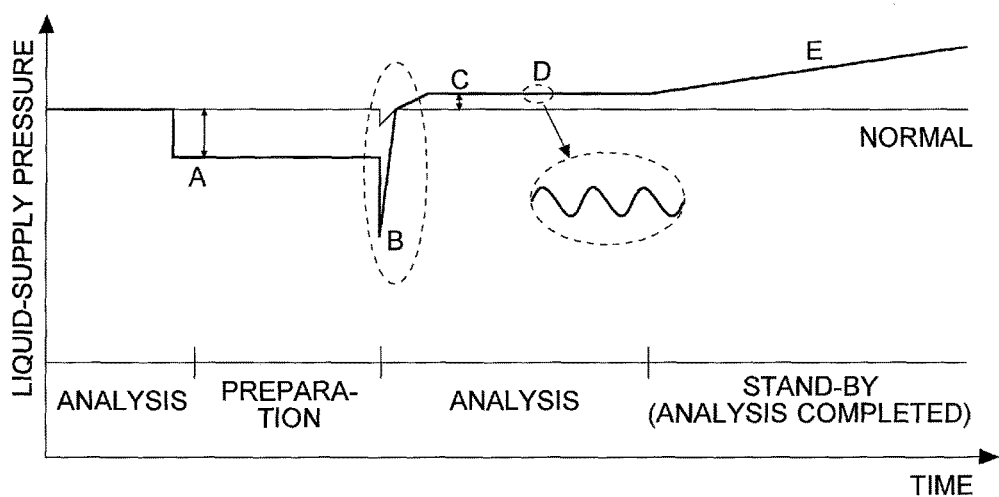
FIG. 3 is a liquid-supply pressure graph illustrating various forms of potentially problematic conditions for the liquid-supply pressure in the liquid chromatograph system.

FIG. 3 shows various changes in the supply pressure of the mobile phase at a position immediately before the column 15 as specific examples of the problems that can occur during the analyzing operation of the liquid chromatograph 10. In FIG. 3, the thin line shows the normal state, while the thick line shows an abnormal case with various problems. In FIG. 3, "A" indicates a pressure drop which occurs when the passage is switched after the completion of the analysis for one sample in order to perform a preparation process (e.g. to suction a new sample or clean the passage) before the analysis for the next sample is initiated. This situation occurs if the valve for switching the passage is considerably worn. If the extent of this pressure drop is still insignificant, it is unnecessary to discontinue the analysis. However, it is preferable to inform users of the occurrence of the pressure drop so that they can take appropriate measures at the next opportunity, such as replacing the valve seal. "B" indicates a pressure drop which occurs at the moment the sample is injected in the injector 14. A slight drop of pressure is inevitable even in the normal case. However, if the magnitude of this pressure drop is large, it is necessary to consider some problem to be present, such as a seal being worn out as in the previous case. "C" is the opposite situation, an increase in the pressure after the sample injection. This situation occurs in the initial phase of the clogging of the passage due to the deposition of the injected sample (or for other reasons). A gradual increase in the pressure, as indicated by "E", can also occur for the same reasons. "D" indicates a periodic fluctuation (pulsation) of the liquid-supply pressure. For example, this situation occurs due to the presence of bubbles in a check valve of the liquid-sending pump 13 or a sealing failure caused by a foreign matter caught in the check valve. By comparing the timing of this pulsation with the rotation angle of the liquid-sending pump 13, it is possible to determine which of the two pumping units 13a and 13b in the liquid-sending pump 13 has the failure of the check valve.

Figure 4:
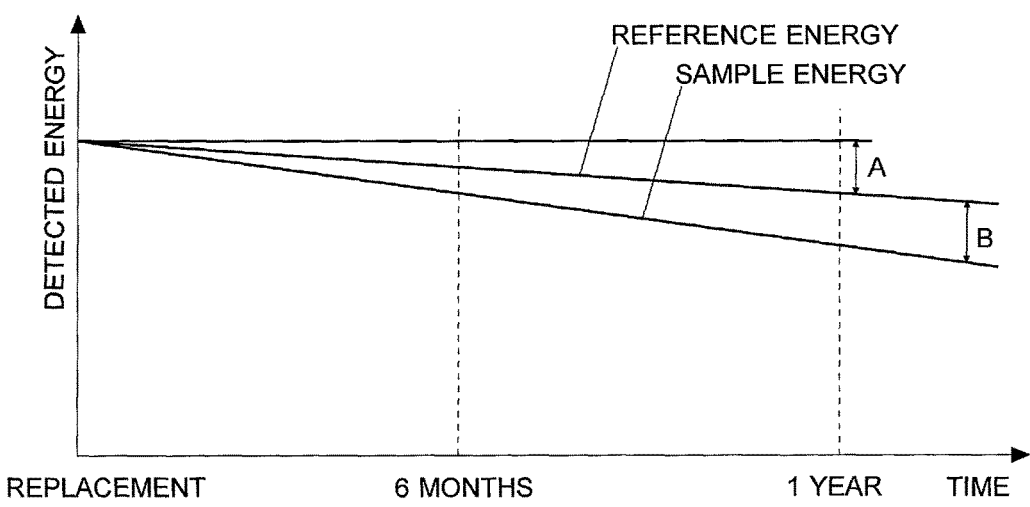
FIG. 4 is a graph showing a long-term change in the energy of the light source of a detector in the liquid chromatograph system.

FIG. 4 is a graph showing the long-term change in the strength (energy) of the light source 18 of the detector 17. Specifically, "A" indicates a decrease in the energy level of the light measured directly without passing through the sample cell 19 ("reference energy"). This decrease can be interpreted as the aging of the light source 18 itself "B" indicates a decrease in the energy level of the light which has passed through the sample cell 19 ("sample energy") If this decrease is detected, it is possible to determine that the sample cell 19 is contaminated.

Based on a predetermined program and a previously stored database, the inference section 23 infers whether or not any section of the liquid chromatograph 10 performing the analyzing operation is in a potentially problematic condition, from the temporal change in the data obtained with the sensors and measurement devices in each section and/or from the combination of two or more of these data. The inferred result is shown on the display device 32. FIG. 6 shows one example. As noted earlier, if a pulsation of the supply pressure of the liquid-sending pump 13 has been detected, the inference section 23 compares the pulsation with the rotation angle of the liquid-sending pump 13 and displays information on the potential problems, such as "Bubbles seem to be present within the right pump head" or "Sealing performance of the right check valve or left-inlet check valve seems to be decreasing." Based on this information, users can take measures against those problems at an appropriate opportunity after the completion of the analysis.

The previous description is concerned with the case where the information on the potential problems is provided during the analyzing operation. Such information is not only useful during the analyzing operation but also in other operations, such as the regular performance check or validation. Accordingly, the information may additionally be displayed during those operations.

As shown in FIG. 6, there is a wide variety of information to be presented to users. As already explained, those kinds of information on the potential problems do not always order prompt suspension of the analysis. Therefore, displaying too much information may actually, prevent users from paying careful attention, which may consequently lead to a delay in taking necessary measures. One solution to this problem is to provide the function of displaying a limited set of information related to a specific theme requested by the user. For example, the display screen shown in FIG. 6 has two selection buttons in its upper right part, labelled as "Poor Reproducibility" and "High Carry-over", which allow users to select one of these themes by clicking the corresponding button using the input device 31. When one of these buttons is clicked, the system displays only the information on the potential problems related to the theme corresponding to the clicked button. The grouping of the information to be displayed according to the user selection can be performed, for example, by using a database (not shown) in which the detection results that may possibly be obtained with the sensors and detection devices are related to the themes to be presented for selection.

REFERENCE SIGNS LIST

10 . . . Liquid Chromatograph
11 . . . Mobile Phase
12 . . . Deaerator
13 . . . Liquid-Sending Pump
14 . . . Injector
15 . . . Column
16 . . . Oven
17 . . . Detector
18 . . . Light Source
19 . . . Sample Cell
25 . . . Spectrophotometer
20 . . . Liquid Chromatograph Control System
21 . . . Controller Section
22 . . . Detection-Measurement Section
23 . . . Inference Section
24 . . . Data Processor Section
31 . . . Input Device
32 . . . Display Device

The invention claimed is:

1. A system configured to monitor and control an operation of a liquid chromatograph which includes a liquid-sending pump configured to send a mobile phase to a column, an injector, disposed between the liquid-sending pump and the column, configured to inject a liquid sample into the mobile phase, and a valve configured to switch a passage of the mobile phase, comprising:
   a) a pressure sensor arranged between the injector and the column to measure a liquid-supply pressure;
   b) an analyzer control system using a computer including a potential problem inference section configured to receive one or more detection results obtained with the pressure sensor and configured to infer a potentially problematic condition that
      b-1) the valve is worn if a pressure drop is observed by the pressure sensor when the passage is switched via the valve;
      b-2) the valve is worn if a pressure drop is observed by the pressure sensor at the moment the liquid sample is injected into the injector;
      b-3) the passage is in an initial phase of clogging due to a deposition of the liquid sample if an increase in the pressure is observed by the pressure sensor after the sample injection; and
      b-4) bubbles present in a check valve of the liquid-sending pump or there is a sealing failure caused by a foreign matter caught in the check valve if a periodic fluctuation in the pressure is observed by the pressure sensor; and
   c) a display screen configured to show at least one of the potentially problematic condition inferred by the potential problem inference section.

2. The system according to claim 1,
   the analyzer control system further including an operational status determiner configured to determine whether or not the liquid chromatograph is performing an analyzing operation including a preparing operation,
   wherein the information on the potentially problematic condition is displayed on the display screen only when the liquid chromatograph is performing an analyzing operation.

3. The system according to claim 1,
   the analyzer control system further including an absolute allowance determiner configured to determine, for each of the one or more detection results obtained with the pressure sensor, whether or not the result is outside a predetermined absolute allowable range,
   wherein the potential problem inference section infers that the liquid chromatograph is in the potentially problematic condition if any of the one or more detection results obtained with the pressure sensor is outside an operationally allowable range which is more narrowly defined than the absolute allowable range.

4. The system according to claim 2,
   the analyzer control system further including an absolute allowance determiner configured to determine, for each of the one or more detection results obtained with the pressure sensor, whether or not the result is outside a predetermined absolute allowable range,
   wherein the potential problem inference section infers that the liquid chromatograph is in the potentially problematic condition if any of the one or more detection results obtained with the pressure sensor is outside an operationally allowable range which is more narrowly defined than the absolute allowable range.

5. The system according to claim 1, further comprising:
   an input section configured to allow a user to perform an input operation; and
   the analyzer control system further including a theme-based status display section configured to show, on the display screen, a group of detection results related to a theme selected through the input section among a plurality of groups of detection results obtained with the pressure sensor where each of the plurality of groups is related to a theme.

6. The system according to claim 2, further comprising:
   an input section configured to allow a user to perform an input operation; and
   the analyzer control system further including a theme-based status display section configured to show, on the display screen, a group of detection results related to a theme selected through the input section among a plurality of groups of detection results obtained with the pressure sensor where each of the plurality of groups is related to a theme.

7. The system according to claim 3, further comprising:
   an input section configured to allow a user to perform an input operation; and
   the analyzer control system further including a theme-based status display section configured to show, on the display screen, a group of detection results related to a theme selected through the input section among a plurality of groups of detection results obtained with the pressure sensor where each of the plurality of groups is related to a theme.

8. The system according to claim 4, further comprising:
   an input section configured to allow a user to perform an input operation; and
   the analyzer control system further including a theme-based status display section configured to show, on the display screen, a group of detection results related to a theme selected through the input section among a plurality of groups of detection results obtained with the pressure sensor where each of the plurality of groups is related to a theme.

9. A method for monitoring and controlling an operation of a liquid chromatograph which includes a liquid-sending pump configured to send a mobile phase to a column, an injector, disposed between the liquid-sending pump and the column, configured to inject a liquid sample into the mobile phase, and a valve configured to switch a passage of the mobile phase, comprising:
   a) detecting a liquid-supply pressure by a pressure sensor arranged between the injector and the column;
   b) receiving one or more detection results obtained with the pressure sensor;
   c) inferring, by using a computer, whether or not the liquid chromatograph is in a potentially problematic condition that
      c-1) the valve is worn if a pressure drop is observed by the pressure sensor when the passage is switched via the valve;
      c-2) the valve is worn if a pressure drop is observed by the pressure sensor at the moment the liquid sample is injected into the injector;
      c-3) the passage is in an initial phase of clogging due to a deposition of the liquid sample if an increase in the pressure is observed by the pressure sensor after the sample injection; and
      c-4) bubbles present in a check valve of the liquid-sending pump or there is a sealing failure caused by a foreign matter caught in the check valve if a periodic fluctuation in the pressure is observed by the pressure sensor; and d) showing, on a display screen, information on the potentially problematic condition.

10. The method according to claim 9, further comprising:

e) determining whether or not the liquid chromatograph is performing an analyzing operation including a preparing operation, and showing, on the display screen, the information on the potentially problematic condition only when the liquid chromatograph is performing an analyzing operation.

11. The method according to claim 9, further comprising:

e) determining, for each of the one or more detection results obtained with the pressure sensor, whether or not the result is outside a predetermined absolute allowable range, and inferring that the liquid chromatograph is in the potentially problematic condition if any of the one or more detection results obtained with the pressure sensor is outside an operationally allowable range which is more narrowly defined than the absolute allowable range.

12. The method according to claim 10, further comprising:

f) determining, for each of the one or more detection results obtained with the pressure sensor, whether or not the result is outside a predetermined absolute allowable range, and inferring that the liquid chromatograph is in the potentially problematic condition if any of the one or more detection results obtained with the pressure sensor is outside an operationally allowable range which is more narrowly defined than the absolute allowable range.

13. The method according to claim 9, further comprising:

e) allowing a user to perform an input operation; and f) showing, on the display screen, a group of detection results related to a theme selected through the input section among a plurality of groups of detection results obtained with the pressure sensor where each of the plurality of groups is related to a theme.

14. The method according to claim 10, further comprising:

f) allowing a user to perform an input operation; and g) showing, on the display screen, a group of detection results related to a theme selected through the input section among a plurality of groups of detection results obtained with the pressure sensor where each of the plurality of groups is related to a theme.

15. The method according to claim 11, further comprising:

f) allowing a user to perform an input operation; and g) showing, on the display screen, a group of detection results related to a theme selected through the input section among a plurality of groups of detection results obtained with the pressure sensor where each of the plurality of groups is related to a theme.

16. The method according to claim 12, further comprising:

g) allowing a user to perform an input operation; and h) showing, on the display screen, a group of detection results related to a theme selected through the input section among a plurality of groups of detection results obtained with the pressure sensor where each of the plurality of groups is related to a theme.

17. A system configured to monitor and control an operation of a liquid chromatograph which includes a liquid-sending pump configured to send a mobile phase to a column, an injector, disposed between the liquid-sending pump and the column, configured to inject a liquid sample into the mobile phase, and a valve configured to switch a passage of the mobile phase, comprising:

a) a pressure sensor arranged between the injector and the column to measure a liquid-supply pressure;

b) an analyzer control system using a computer including a potential problem inference section configured to receive one or more detection results obtained with the pressure sensor and configured to infer a potentially problematic condition that b-1) the valve is worn if a pressure drop is observed by the pressure sensor when the passage is switched via the valve; and c) a display screen configured to show at least one of the potentially problematic condition inferred by the potential problem inference section.

18. A system configured to monitor and control an operation of a liquid chromatograph which includes a liquid-sending pump configured to send a mobile phase to a column, an injector, disposed between the liquid-sending pump and the column, configured to inject a liquid sample into the mobile phase, and a valve configured to switch a passage of the mobile phase, comprising:

a) a pressure sensor arranged between the injector and the column to measure a liquid-supply pressure;

b) an analyzer control system using a computer including a potential problem inference section configured to receive one or more detection results obtained with the pressure sensor and configured to infer a potentially problematic condition that b-2) the valve is worn if a pressure drop is observed by the pressure sensor at the moment the liquid sample is injected into the injector; and c) a display screen configured to show at least one of the potentially problematic condition inferred by the potential problem inference section.

19. A system configured to monitor and control an operation of a liquid chromatograph which includes a liquid-sending pump configured to send a mobile phase to a column, an injector, disposed between the liquid-sending pump and the column, configured to inject a liquid sample into the mobile phase, and a valve configured to switch a passage of the mobile phase, comprising:

a) a pressure sensor arranged between the injector and the column to measure a liquid-supply pressure;

b) an analyzer control system using a computer including a potential problem inference section configured to receive one or more detection results obtained with the pressure sensor and configured to infer a potentially problematic condition that b-4) bubbles present in a check valve of the liquid-sending pump or there is a sealing failure caused by a foreign matter caught in the check valve if a periodic fluctuation in the pressure is observed by the pressure sensor; and c) a display screen configured to show at least one of the potentially problematic condition inferred by the potential problem inference section.

* * * * *